(12) United States Patent
Van Groenestijn et al.

(10) Patent No.: US 10,954,532 B2
(45) Date of Patent: Mar. 23, 2021

(54) PROCESS FOR THE PRODUCTION OF BIOGAS

(75) Inventors: Johannes Wouterus Van Groenestijn, Apeldoorn (NL); Gijsbert Maurits Bos, Apeldoorn (NL)

(73) Assignee: STICHTING WAGENINGEN RESEARCH, Wageningen (NL)

( * ) Notice: Subject to any disclaimer, the term of this patent is extended or adjusted under 35 U.S.C. 154(b) by 816 days.

(21) Appl. No.: 12/444,516

(22) PCT Filed: Oct. 10, 2007

(86) PCT No.: PCT/NL2007/050492
§ 371 (c)(1),
(2), (4) Date: Apr. 6, 2009

(87) PCT Pub. No.: WO2008/044929
PCT Pub. Date: Apr. 17, 2008

(65) Prior Publication Data
US 2010/0015680 A1    Jan. 21, 2010

(30) Foreign Application Priority Data
Oct. 10, 2006  (EP) ..................... 06076862

(51) Int. Cl.
*C12P 5/02* (2006.01)
(52) U.S. Cl.
CPC .............. *C12P 5/023* (2013.01); *Y02E 50/30* (2013.01)
(58) Field of Classification Search
USPC ....................................................... 435/167
See application file for complete search history.

(56) References Cited

U.S. PATENT DOCUMENTS

| | | | |
|---|---|---|---|
| 1,880,773 A * | 10/1932 | Buswell .................. | C12M 21/04 210/194 |
| 4,237,226 A * | 12/1980 | Grethlein ................ | C12P 19/20 127/29 |
| 4,696,746 A * | 9/1987 | Ghosh et al. ................. | 210/603 |
| 4,735,724 A * | 4/1988 | Chynoweth ............... | C02F 3/28 210/180 |
| 5,221,357 A | 6/1993 | Brink | |
| 5,705,369 A * | 1/1998 | Torget ..................... | C08H 8/00 127/1 |
| 5,837,506 A * | 11/1998 | Lynd ........................ | C12P 7/10 435/165 |
| 6,342,378 B1 | 1/2002 | Zhang et al. | |
| 2002/0079266 A1* | 6/2002 | Ainsworth ................ | C02F 3/28 210/603 |
| 2002/0148778 A1* | 10/2002 | Raven .................... | C12M 21/04 210/603 |
| 2003/0141243 A1 | 7/2003 | Groenestijin et al. | |
| 2006/0275895 A1 | 7/2006 | Jensen et al. | |

FOREIGN PATENT DOCUMENTS

GB    349032    *    5/1931

OTHER PUBLICATIONS

Margosch et al. (Applied and Environmental Microbiology, vol. 72, No. 5, pp. 3476-3481; 2006).*
Ohwaki et al. (Applied and Environmental Microbiology, vol. 33, No. 6, pp. 1270-1274; 1977).*
Ohwaki et al. (Applied and Environmental Microbiology, vol. 33, No. 6, pp. 1270-1274; 1977) of record.*
Baugh, K. D., et al: "Thermochemical pretreatment of lignocellulose to enhance methane fermentation II. Evaluation and application of pretreatment model", 1988, Biotechnology and Bioengineering, vol. 31, pp. 62-70, 1988.
Office Action issued in corresponding European Patent Application No. 07834630.1 and dated Jun. 10, 2011.

* cited by examiner

*Primary Examiner* — Soren Harward
*Assistant Examiner* — Paul D. Pyla
(74) *Attorney, Agent, or Firm* — Lucas & Mercanti, LLP

(57) ABSTRACT

The invention relates to a process for the production of biogas from biomass, in particular from lignocellulose-containing biomass. According to the invention bio gas is produced from lignocellulose-containing biomass in a process, wherein the cellulose and hemicellulose in the lignocellulose are made accessible for bioconversion.

20 Claims, 1 Drawing Sheet

PROCESS FOR THE PRODUCTION OF BIOGAS

The invention relates to a process for the production of biogas from biomass, in particular from lignocellulose-containing biomass.

Combustible renewables are playing an increasingly important role in today's world. Valuable products, such as methane, can be produced from renewable starting materials, such as biomass, by biological conversion processes.

The term biogas as used herein refers to a gas comprising methane and optionally also carbon dioxide. A sustainable way of obtaining biogas is by the anaerobic digestion of biomass. One of the problems faced in anaerobic digestion of biomass is that lignin and lignocellulose remain stable under anaerobic conditions and thus cannot be converted. Lignocellulose is a complex fibrous structure of the sugar polymers cellulose and hemicellulose, strongly intermeshed with the aromatic copolymer lignin. Both lignin and lignocellulose are very abundant biopolymers and are present in most forms of biomass.

The presently available anaerobic digestion processes for producing biogas, for instance the process known from WO-A-2004/016796, fail to efficiently convert the valuable carbohydrates which remain captured within the lignocellulose complex. This results in a lower conversion efficiency to valuable biogas. As a result, the anaerobic digestion processes also typically result in a considerable amount of invaluable non-converted residue.

In WO-A-2005/000748 it is suggested to anaerobically hydrolyse material that has not been digested in the digestion reactor in order to make the material available for bacterial digestion. However, at low temperatures the fractionation and hydrolysis of lignocellulose will be very incomplete, and at long reaction times the amount of inhibitory by-products (furfural and 5-hydroxymethylfurfural) produced will be high. Moreover, the present inventors found that the results still strongly depend on the pH applied. At a pH higher than 7, the fractionation is very poor.

U.S. Pat. No. 5,221,357 describes the hydrolysis of lignocellulose in two steps. In the first step hemicellulose is hydrolysed at a temperature of 140-220° C. at a pH of between 1.4 and 3. The second step is a purely chemical process in which cellulose is hydrolysed at temperatures of 160-240° C. At such high temperatures microbiological activity is not possible. This document does not describe an anaerobic digestion step.

U.S. Pat. No. 5,705,369 describes the pre-hydrolysis of lignocellulose, in which lignocellulosic feedstock is subjected to a pre-hydrolysis at 90-240° C. and a pH of 1.0-5.5. This document does not describe anaerobic digestion to produce biogas.

Object of the invention is to provide a process for the production of biogas in which the biogas yield is increased and at the same time the amount of non-converted residue is reduced.

The inventors found that this object can be met by producing biogas from lignocellulose-containing biomass in a process, wherein the cellulose and hemicellulose in the lignocellulose are made accessible for bioconversion. Accordingly, the invention is directed to the production of biogas from a feed stream of lignocellulose-containing biomass comprising the steps of:
i) subjecting the biomass stream to a temperature of 150-250° C. at a pH of 3-7; and
ii) subjecting the product of step i) to anaerobic digestion, thereby producing a stream of biogas.

Surprisingly, it was found that the process of the invention enables to set the lignocellulose complex free and to fractionate the lignocellulose into accessible cellulose and hemicellulose, which can be further hydrolysed and converted into biogas in an anaerobical biological digester. Hydrolysis is not required in the acid thermal treatment step i) as the hydrolysis takes place in the anaerobical digester. In comparison to the state of the art the process of the invention therefore results in a considerable increase in biogas production and a reduction of invaluable non-converted residue.

As starting material any lignocellulose-containing biomass can be used including agricultural wastes (such as corn stover, wheat straw, rice straw, seed hulls, sugarcane leavings, bagasse, nutshells, and manure (e.g. from cattle, poultry, and hogs)), wood materials (such as wood or bark, sawdust, timber slash, and mill scrap), municipal waste (such as waste paper and yard clippings), and energy crops (such as poplars, willows, switchgrass, alfalfa, prairie bluestem, corn, beets, and soybean).

The feed stream of lignocellulose-containing biomass is preferably in the form of a slurry. Typically this slurry has a solid contents of 1-50 wt. %, preferably 5-35 wt. %. Such slurry can be produced by cutting and grinding the biomass and mixing it with water.

Figure 1:
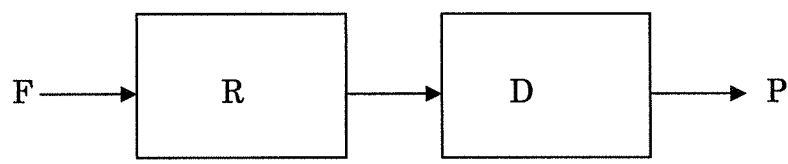
FIG. 1 is a schematic representation of the process for producing biogas from lignocellulose-containing biomass.

FIG. 1 is a schematic representation of the process of the present invention. The lignocellulose-containing biomass (F) is subjected to a step wherein it is brought at elevated temperatures at an acid pH (R), so that lignocellulose is at least partly released, and subsequently fed into an anaerobic digester (D), from which the biogas product (P) is obtained.

Figure 2:
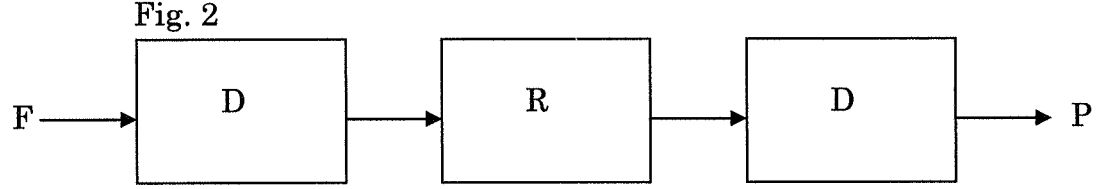
FIG. 2 is a schematic representation of an alternate process depicting in which a second digester is employed.
Figure 3:
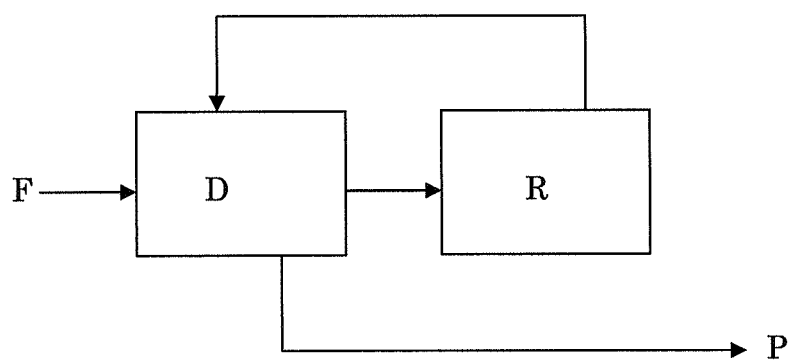
FIG. 3 is a schematic representation of a third process for producing a biogas illustrating a recycle stream.

In one embodiment of the present invention, which embodiment is particularly useful in case of bulky biomass feeds with a low fraction of lignocellulose (e.g. lower than 10 wt. %) the raw material is first fed to a digester (D) so that it is anaerobically digested and subsequently to a step wherein the lignocellulose is released (R), followed by a step (D) as explained above. This embodiment can be carried out in different ways. In FIG. 2, two different digesters D are depicted. It is however, particularly advantageous to use the configuration of FIG. 3, wherein the digesting step is the same as step ii), which then has to be extended with a recycle stream for recycling the product to step i). The recycle stream may be subjected to a concentration step (e.g. by filtration or centrifugation) before feeding it to the thermal treatment of step i). The biomass leaving step i) is subsequently fed to step ii).

In step i) of the process according to the invention the pH is kept at 3-7, preferably 3.5-6, more preferably 4-5. The pH may be lowered by adding an organic acid, such as formic acid, lactic acid or acetic acid. Sulphuric acid and phosphoric acid may also be used, but are not preferred. Sulphuric acid is converted in the anaerobic digestion step into sulphide, which in turn inhibits the anaerobic digestion to methane. Therefore, the amount of sulphide in step i) is preferably at most 1000 mg/l, more preferably at most 500 mg/l. The addition of phosphoric acid leads to the production of undesirable phosphates.

Lowering the pH with organic acids instead of inorganic acids is advantageous, because organic acids are also converted into biogas. Furthermore, most inorganic acids have intrinsic disadvantages: sulphuric acids can result in the production of toxic sulphides, nitric acid can inhibit the methanogenic activity due to an increase of the redox potential, the use of hydrochloric acids can lead to corrosion and undesirable environmental effects, and phosphoric acid may cause undesirable environmental effects.

During the thermal fractionation of lignocellulose acetic acid is released from hemicellulose, which contributes to a lowering of the pH.

The temperature in step i) of the process according to the invention is 150-250° C., preferably 160-220° C. At these high temperatures the cellulose, hemicellulose and lignin are fractionated so that cellulose and hemicellulose become accessible for biological degradation. Furthermore, a large part of the hemicellulose is hydrolysed at these temperatures. Temperatures above 250° C. result in undesirable by-products that inhibit anaerobic digestion. If the temperature is below 150° C., the lignocellulose is insufficiently fractionated. Typically, the temperature is about 190° C. It is preferred that the biomass is mixed well, so that the temperature may be lowered. The energy which is required for this heating is preferably obtained from the exhaust gases of device or installation which is fed with the biogas.

Step i) is generally carried out at elevated pressure. The pressure in step i) is preferably equal to, or higher than the saturation vapour pressure at the used (high) temperature.

Step i) of the process according to the invention is typically carried out for a few minutes, typically 2-15 minutes, more preferably 3-5 minutes. Longer reaction times lead to the production of undesirable by-products, such as furfural and 5-hydroxymethylfurfural.

Step i) can be carried out in a plug flow heat exchanger or in a Continuous Stirred Tank Reactor (CSTR) in which the time the slurry has a temperature higher than 150° C. can be adjusted accurately. It was found that only minor amounts of by-products are obtained when using fast heating and cooling of the slurry.

Although not necessary, the biomass leaving step i) can be cooled before entering step ii), in the embodiment wherein step i) is followed by step ii). The released heat may be usefully recovered.

In step ii) of the process according to the invention the biomass is digested. During the anaerobic digestion process, organic nitrogen compounds are converted to ammonia, sulphur compounds are converted to hydrogen sulphide, phosphorus to orthophosphates, and calcium, magnesium, and sodium are converted to a variety of salts. Through proper operation, the inorganic constituents can be converted to a variety of beneficial products. The obtained biogas can be used as fuel.

The anaerobic digestion is carried out by a group of micro-organisms working together to convert organic matter to gas and inorganic constituents. The first step of anaerobic digestion is the breakdown of particulate matter to soluble organic constituents that can be processed through the bacterial cell wall. Hydrolysis, or the liquefaction of insoluble materials, is the rate-limiting step in anaerobic digestion of waste slurries. This step is carried out by a variety of bacteria through the excretion of extra-cellular enzymes that reside in close proximity to the bacteria. The soluble organic materials that are produced through hydrolysis consist of sugars, fatty acids, and amino acids. Those soluble constituents are converted to carbon dioxide and a variety of short chain organic acids by acid forming bacteria.

Other groups of bacteria reduce the hydrogen toxicity by scavenging hydrogen to produce ammonia, hydrogen sulphide, and methane. A group of methanogens converts acetic acid to methane gas. A wide variety of physical, chemical, and biological reactions take place.

The bacteria that are responsible for the anaerobic digestion require a sufficient concentration of nutrients to achieve optimum growth. The carbon to nitrogen ratio in the waste is preferably less than 43. The carbon to phosphorus ratio is preferably less than 187.

The anaerobic digestion of step ii) of the process according to the invention is preferably carried out at a temperature of 20-40° C., preferably 30-38° C. Thermophilic digestion using a temperature of 45-70° C. is another option, which combines very well with the thermal pre-treatment described. Preferably, the temperature in the anaerobic digestion step ii) is at most 100° C., preferably at most 80° C., more preferably at most 70° C., in order to create conditions at which considerable microbiological activity is possible.

The pH in the anaerobic digestion step ii) may be between 6 and 9. The higher pH in comparison to the pH used in the thermal treatment step i) is attained as a result of the biodegradation of organic acids or the conversion of sulphuric acid (a strong acid) into hydrogen sulphide (a weak acid). In order to have good results with respect to anaerobic digestion, it is preferred that the pH in step ii) is at least 5, preferably at least 6.

An additional advantage of the invention is that the addition of enzymes, such as cellulase, is not required. The anaerobic digestion into biogas is carried out in the presence of micro-organisms which already excrete these hydrolytic enzymes. Hydrolytic enzymes are for instance excreted by strict or facultative anaerobic acidogenic bacteria, such as Clostridium.

In a preferred embodiment, the process of the invention is carried out prior to an electricity generator or a thermal power station.

The invention claimed is:

1. Process for the production of biogas from a feed stream of lignocellulose-containing biomass comprising the steps of:
   i) pre-treating a feed stream of lignocellulose-containing biomass, carried out for at least 2 minutes in a plug flow heat exchanger, by subjecting the feed stream of lignocellulose-containing biomass to a temperature of 150-250° C. at a pH of 3.0-7.0 in the presence of an organic acid and the substantial absence of sulfuric acid, wherein hydrolysis is not required, and wherein the lignocellulose is fractionated to obtain a pre-treated product comprising fractionated cellulose and hemicellulose; and
   ii) feeding the pre-treated product of step i) as a whole to an anaerobic digester in which the pre-treated product as a whole is subjected to anaerobic digestion in the presence of micro-organisms which excrete hydrolytic enzymes, wherein the cellulose and hemicellulose are hydrolyzed thereby producing a stream of biogas,
   wherein the biomass leaving step i) is cooled before entering step ii).

2. Process according to claim 1 further comprising a pre-treatment step, wherein a stream of biomass containing a low fraction of lignocellulose is first fed to a digester wherein it is subjected to anaerobic digestion to produce the feed stream that is fed to step i).

3. Process according to claim 2, wherein said anaerobic digestion is carried out as in step ii).

4. Process according to claim 1, wherein the pH in step i) is 4-5.

5. Process according to claim 1, wherein the temperature in step i) is 160-220° C.

6. Process according to claim 1, wherein an amount of sulphide is obtained in step i) and is at most 1000 mg/l.

7. Process according to claim 1, wherein an amount of sulphide is obtained in step i) and is at most 500 mg/l.

8. Process according to claim 1, wherein step i) lasts from 2-15 minutes.

9. Process according to claim 1, wherein step i) is carried out at a pressure equal to or higher than a saturation vapor pressure at a used temperature.

10. Process according to claim 1, wherein step ii) is carried out at a temperature of 20°-40° C.

11. Process according to claim 1, wherein step ii) is carried out at a temperature of 45°-70° C.

12. Process according to claim 1, wherein step ii) is carried out at a temperature of 70°–100° C.

13. Process according to claim 1, wherein the pH in step ii) is between 6-9.

14. Process according to claim 1, wherein the pH in step ii) is at least 5.

15. Process according to claim 1, wherein the pH in step ii) is at least 6.

16. Process for the production of biogas from a feed stream of lignocellulose-containing biomass comprising the steps of:
   i) pre-treating a feed stream of lignocellulose-containing biomass, carried out for at least 2 minutes in a Continuous Stirred Tank Reactor (CSTR), by subjecting the feed stream of lignocellulose-containing biomass to a temperature of 150-250° C. at a pH of 3.0-7.0 in the presence of an organic acid and the substantial absence of sulfuric acid, wherein hydrolysis is not required, and wherein the lignocellulose is fractionated to obtain a pre-treated product comprising fractionated cellulose and hemicellulose; and
   ii) feeding the pre-treated product of step i) as a whole to an anaerobic digester in which the pre-treated product as a whole is subjected to anaerobic digestion in the presence of micro-organisms which excrete hydrolytic enzymes, wherein the cellulose and hemicellulose is hydrolyzed thereby producing a stream of biogas,
   wherein the biomass leaving step i) is cooled before entering step ii).

17. Process according to claim 16, further comprising a pre-treatment step, wherein a stream of biomass containing a low fraction of lignocellulose is first fed to a digester wherein it is subjected to anaerobic digestion to produce the feed stream that is fed to step i).

18. Process according to claim 17, wherein said anaerobic digestion is carried out as in step ii).

19. Process according to claim 16, wherein the pH in step i) is 4-5.

20. Process according to claim 16, wherein the temperature in step i) is 160-220° C.

* * * * *